(12) United States Patent
Carroll et al.

(10) Patent No.: US 7,928,234 B2
(45) Date of Patent: Apr. 19, 2011

(54) CONVERSION OF THEBAINE TO MORPHINE DERIVATIVES

(75) Inventors: Robert James Carroll, St. Catharines (CA); Hannes Leisch, St. Catharines (CA); Tomas Hudlicky, St. Catharines (CA)

(73) Assignee: Brock University, Ontario (CA)

( * ) Notice: Subject to any disclaimer, the term of this patent is extended or adjusted under 35 U.S.C. 154(b) by 844 days.

(21) Appl. No.: 11/771,259

(22) Filed: Jun. 29, 2007

(65) Prior Publication Data

US 2009/0005563 A1 Jan. 1, 2009

(51) Int. Cl.
*C07D 489/02* (2006.01)
*C07D 489/08* (2006.01)
(52) U.S. Cl. .......................................... 546/45; 546/44
(58) Field of Classification Search ............... 546/45, 546/39, 44
See application file for complete search history.

(56) References Cited

U.S. PATENT DOCUMENTS 4,277,604 A 7/1981 Dauben
5,668,285 A 9/1997 Rice

FOREIGN PATENT DOCUMENTS

WO 2006/138020 12/2006

OTHER PUBLICATIONS

Leisch, H. et al.: Studies on regioselective hydrogenation of thebaine and its conversion to hydrocodone. Tetrahed. Lett., vol. 48, pp. 3979-3981, 2007.*
Barber, et al, "*Conversion of Thebaine to Codeine*", J. Med. Chem. vol. 19, No. 10, 1996, pp. 1175-1180.
Osa, et al, "*A New Useful Conversion Method of Naltrexone to 14-Deoxynaltrexone*", Heterocycles, vol. 69, 2006, pp. 271-282.

* cited by examiner

*Primary Examiner* — Charanjit S Aulakh
(74) *Attorney, Agent, or Firm* — Occhiuti Rohlicek & Tsao LLP

(57) ABSTRACT

The present invention provides methods for the conversion of thebaine to a morphine derivative, such as hydrocodone. Novel ketal intermediates of the conversion are provided. A one-pot procedure for the conversion comprises treating thebaine with an acid in the presence of a metal catalyst.

27 Claims, No Drawings

CONVERSION OF THEBAINE TO MORPHINE DERIVATIVES

FIELD OF INVENTION

The present invention relates to morphine-derived products. In particular, the invention relates to novel intermediates and methods for the synthesis of morphine derivatives.

BACKGROUND OF THE INVENTION

The supply of morphine and morphine-derived products in medicine depends on the isolation of major constituents of the opium poppy such as morphine 1, codeine 2 and thebaine 3, the structures of which are shown below.

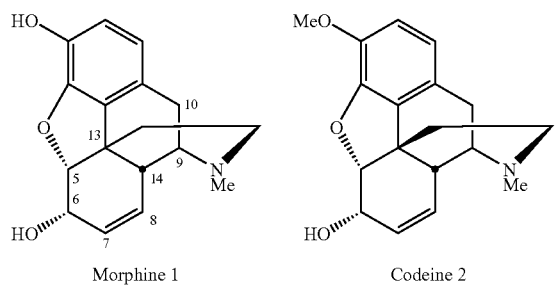

Morphine 1          Codeine 2

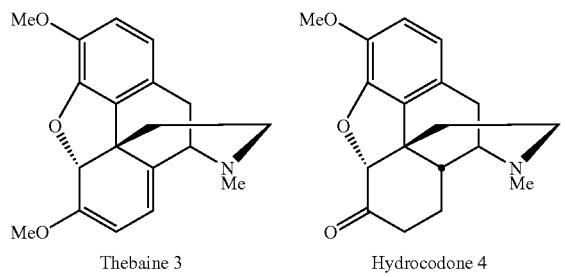

Thebaine 3          Hydrocodone 4

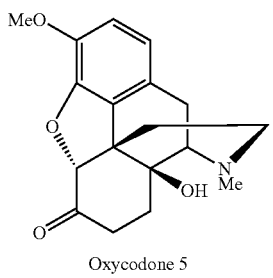

Oxycodone 5

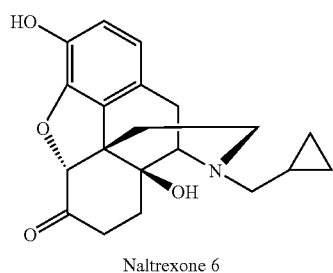

Naltrexone 6

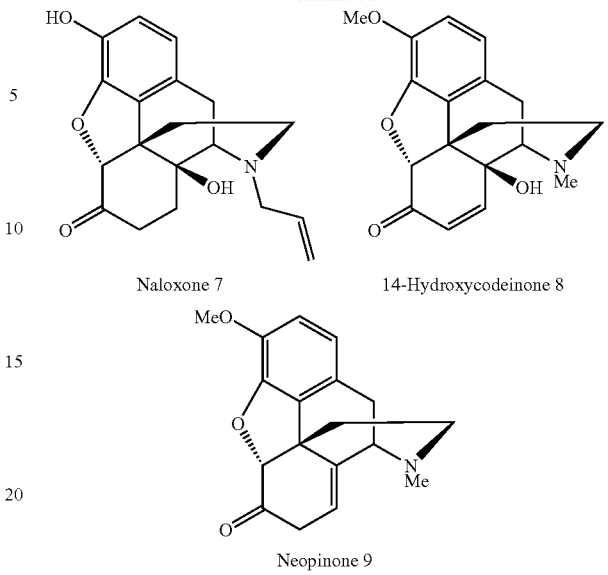

Naloxone 7          14-Hydroxycodeinone 8

Neopinone 9

The alkaloids are then converted by semi-synthesis to other medicinally useful agents such as hydrocodone 4, oxycodone 5, naltrexone 6, and naloxone 7.

Because of the commercial importance of these products, many attempts have been made to find an efficient method for their production. For example, United States Patent Application 2006/0167258 discloses a process for the manufacture of dihydrothebaine, dihydrocodeinone enol acetate, hydrocodone, and analogs thereof by reacting dihydrocodeine or analogs thereof with benzophenone in the presence of potassium tert-alkylate in a hydrocarbon solvent to generate a reaction mixture containing an enolate of the corresponding ketone, followed by addition of the reaction mixture to the electrophilic agent and isolation of the product. United States Patent No. 2006/0074239 discloses a method for the catalytic conversion of codeine, morphine or analogs thereof into hydrocodone, hydromorphone or analogs thereof utilizing a transition metal complex of a tertiary phosphine halide as catalyst. United States Patent Application 2003/0045720 discloses a method for the production of hydromorphone and hydrocodone from an alkaloid that comprises mixing the narcotic alkaloid with an acid in the presence of a catalyst wherein the method is carried out in the substantial absence of hydrogen gas. U.S. Pat. No. 5,571,685 discloses a method for the production of hydrocodone from neopinone or codeinone involving a morphinone reductase enzyme. Methods for the production of other derivatives can be found, for example, in U.S. Pat. Nos. 6,235,906; 6,291,675; 6,864,370 and 7,129,248.

Thebaine is a particularly useful opiate alkaloid that can be converted into a variety of compounds such as hydrocodone, oxycodone, oxymorphone, nalbuphine, naloxone, naltrexone, buprenorphine and etorphine. The use of thebaine as a precursor alkaloid has been limited by the fact that it is a minor constituent of the latex obtained from the opium poppy. However, with the advent of genetically engineered plants, the content of thebaine in the latex may exceed 30%. Thebaine can be isolated as a major component from genetically altered plants introduced by Tasmanian Alkaloids and described in U.S. Pat. No. 6,067,749.

Since thebaine can now be isolated in significant amounts, it could be an ideal starting material for the semi-synthetic opioid derivatives, such as hydrocodone and oxycodone. However, conversion of thebaine to the derivatives using current methods results in the production of undesirable intermediates. Recent recommendations from the ICH (International Conference on Harmonisation) recommend that the amount of α, β-unsaturated ketone containing compounds should be limited in pharmaceutical preparations (ICH Safety Guidelines, ICH S2A, 1995: ICH S2B, 1997). Thus, there has been an unmet need for new methods for the synthesis of morphine derivatives that avoid the production of such intermediates/impurities and that are cost efficient.

SUMMARY OF THE INVENTION

The present invention addresses the need for new methods for the synthesis of active morphine derivatives. According to the methods of the invention, thebaine is converted to a derivative such as hydrocodone. Variations of the method may also be used to convert thebaine to a C14 hydroxylated derivative. Novel ketal intermediates derived from thebaine are provided. These ketal intermediates play an important role in the conversion of thebaine to an active morphine derivative. A one pot method for the conversion of thebaine to hydrocodone is also provided.

In a first aspect of the invention, a method of converting thebaine to a morphine derivative is provided. The method comprises the steps of: combining thebaine with an organic compound having at least one hydroxyl group in the presence of a catalyst to obtain a ketal intermediate; exposing the ketal intermediate to hydrogenation to obtain a hydrogenated intermediate; and hydrolyzing the hydrogenated intermediate to obtain a morphine derivative. Preferred morphine derivatives include hydrocodone and oxycodone, more preferably hydrocodone.

In a preferred embodiment, the hydrogenation and hydrolyzation steps are combined in a one-pot procedure.

Various types of organic compounds can be used in the methods of the invention. For example, the organic compound may be an aliphatic alcohol other than methanol or it may be a diol such as ethylene glycol or 2,3-dimethyl-1,4-butane diol.

In one preferred embodiment the catalyst is a protic or Lewis acid. A preferred acid catalyst is p-toluenesulfonic acid.

In another preferred embodiment, the catalyst is a metal catalyst. The catalyst is usually selected from the group consisting of: Pd, Pd(OAc)$_2$, PdCl$_2$, PdBr$_2$, PdO, RhCl$_3$, PtO$_2$, RhCl(PPh$_3$)$_3$, Rh/Al, Pd/C, Pt/C, Pd on CaCO$_3$/Pb, Pd/Al, PtCl$_2$, PtCl$_4$, Al, Zn, Fe, Sn, Ru, Co, Rh, Ir, Ni, Pd, Pt, Ti, Os, Cu. Preferred catalysts include Pd(OAc)$_2$, PdCl$_2$, PdBr$_2$, PdO, RhCl$_3$, PtO$_2$, RhCl(PPh$_3$)$_3$, Rh/Al, Pd/C, Pt/C, Pd on CaCO$_3$/Pb (Lindlar), Pd/Al, PtCl$_2$, PtCl$_4$.

In another aspect of the invention, a ketal derivative obtained according to the methods of the invention is provided.

In a preferred embodiment, a ketal derivative of thebaine comprises a structure selected from the group below:

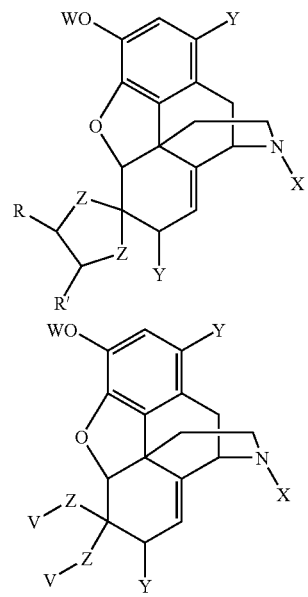

wherein V is $C_2$-$C_{10}$ alkyl

W is H or $C_1$-$C_{10}$ alkyl

X is H or $C_1$-$C_{10}$ alkyl, cyclopropylmethyl, cyclobutylmethyl, propenyl, acyl (C1-C10) or carboxy (C1-C10)

Y is H or I or Br or Cl or F

R is H, alkyl (C1-C10), hydroxyl alkyl (C1-C10), or alkoxy alkyl;

R$_1$ is H, alkyl (C1-C10), hydroxyl alkyl (C1-C10), or alkoxy alkyl;

Z is O, S or N; and wherein R and R1 may be the same or different.

Preferred ketal intermediates include the compounds shown below:

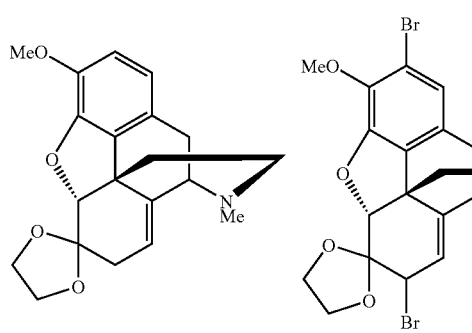

In a preferred embodiment the ketal derivative is an unsaturated ethylene glycol ketal of neopinone.

In another preferred embodiment, the ketal derivative is a halogenated ketal.

In another aspect of the invention, a hydrogenated ketal intermediate is provided.

In a preferred embodiment, the hydrogenated intermediate has the structure:

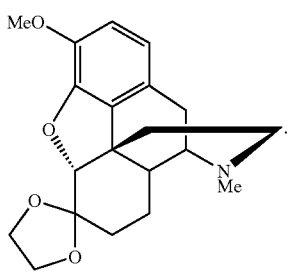

In yet another aspect of the invention, an alkyl ammonium salt of the ketal intermediate is provided.

In preferred embodiments, the salt is allyl derived or methylene cyclopropyl derived.

In a further aspect of the invention, a method of obtaining a morphine derivative from thebaine is provided. The method comprises: combining thebaine with an organic compound having at least one hydroxyl group in the presence of a pseudo-proton to obtain a ketal intermediate; and subjecting the intermediate to a one pot hydrogenation and hydrolysis to obtain the morphine derivative, preferably hydrocodone.

In a preferred embodiment, the pseudo proton is provided by a halogen selected from the group consisting of bromine, chlorine and iodine, preferably bromine.

In another preferred embodiment, the pseudo proton is provided by a transition metal catalyst.

In yet another aspect of the invention, a one pot method of obtaining hydrocodone from thebaine is provided that comprises exposing thebaine to $Pd(OAc)_2$ in the presence of an organic compound having at least one hydroxyl group. The organic compound having at least one hydroxyl group is preferably ethylene glycol.

In a further aspect of the invention a one pot method for the conversion of thebaine to hydrocodone comprises exposing thebaine to $Pd(OAc)_2$ in the presence of aqueous THF followed by hydrogenation.

In a further aspect, a one-pot method for obtaining hydrocodone from thebaine comprising exposing thebaine to an acid under about one atmosphere of hydrogen in the presence of a catalyst under aqueous conditions is provided. The acid typically comprises HCl or $H_2SO_4$.

In another aspect of the invention, a method of converting thebaine to a C14 hydroxylated derivative, said method comprising the steps of:
  i) exposing thebaine to an organic compound containing at least one hydroxyl group in the presence of a catalyst to obtain a ketal intermediate; subjecting the derivative to hydrogenation and hydrolysis; and
  ii) oxidation of a hydrogen to a hydroxyl.

In a further aspect, there is provided a method of converting thebaine to a C14 hydroxylated derivative. The method comprises the steps of: exposing thebaine to an organic compound containing at least one hydroxyl group in the presence of a catalyst to obtain a ketal intermediate; converting the ketal to a 14-hydroxy ketal; and subjecting the 14-hydroxyketal to hydrolysis.

DETAILED DESCRIPTION

The present invention provides methods for the production of hydrocodone and analogs thereof using thebaine ($C_{19}H_{21}NO_3$) as the starting material. The methods of the invention allow for the production of morphine derivatives in a rapid and cost-efficient manner.

While hydrocodone is a preferred ketone derivative obtained according to the methods of the invention, slight variations in the methods may yield other derivatives, such as oxycodone, naltrexone, naloxone, 14-hydroxycodeinone, neopinone, hydromorphone, and oxymorphone. The invention encompasses the production of these other derivatives from thebaine as well as novel derivatives obtained using the methods of the invention.

Methods of the invention for the conversion of thebaine to a ketone derivative may include the synthesis of a ketal intermediate, followed by hydrogenation and then hydrolysis. Alternatively, a one-pot procedure for the conversion of thebaine to hydrocodone may be used. Preferred embodiments of the methods are discussed below.

In a first aspect of the invention, thebaine is combined with an organic compound having at least one hydroxyl group, other than methanol, in the presence of catalyst and a novel ketal derivative is produced. The nature of the ketal derivative varies depending on the alcohol used. For example, exposure of thebaine to a 1, 2 diol leads to the generation of a β, γ, unsaturated ketal intermediate.

An exemplary reaction scheme is shown below:

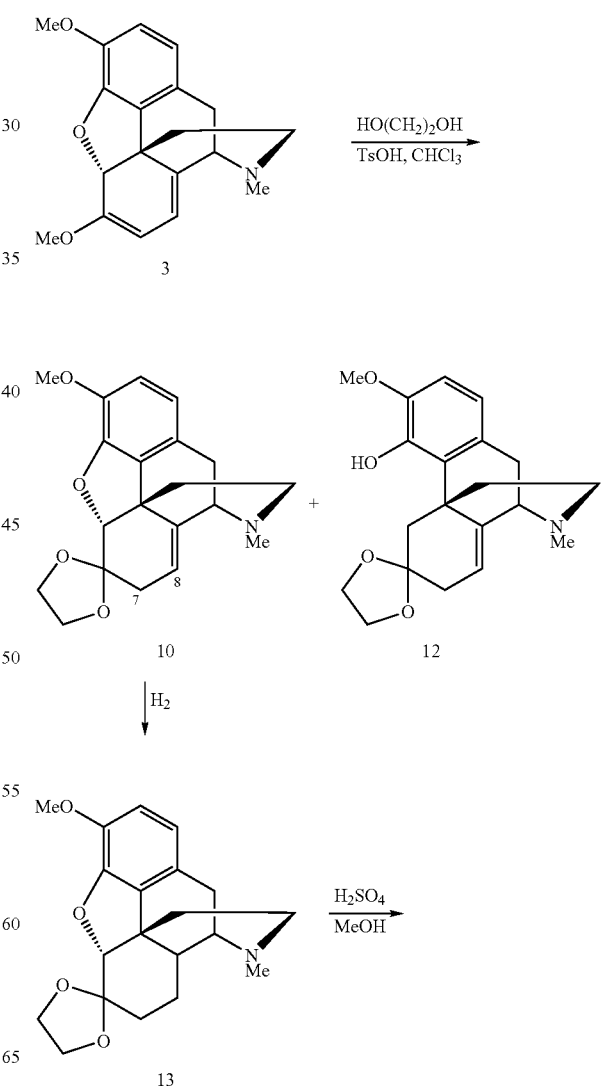

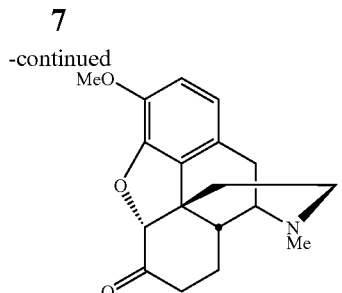

4

Exposure of thebaine 3 to ethylene glycol in chloroform in the presence of TsOH led to smooth conversion to the corresponding ketal 10.

The $\Delta_{7-8}$ isomeric ketal was not detected in the reaction mixture. The ketal intermediate 10 was converted to a hydrogenated intermediate 13 under 1 atmosphere of hydrogen. Subsequent hydrolysis resulted in the production of hydrocodone 4. Ketal 10 can also be directly converted to 4 using a one pot hydrogenation and hydrolysis procedure.

Alternative conditions for the collapse of the enol ether of thebaine in order to generate 10 were also investigated. Several exemplary reactions are shown below.

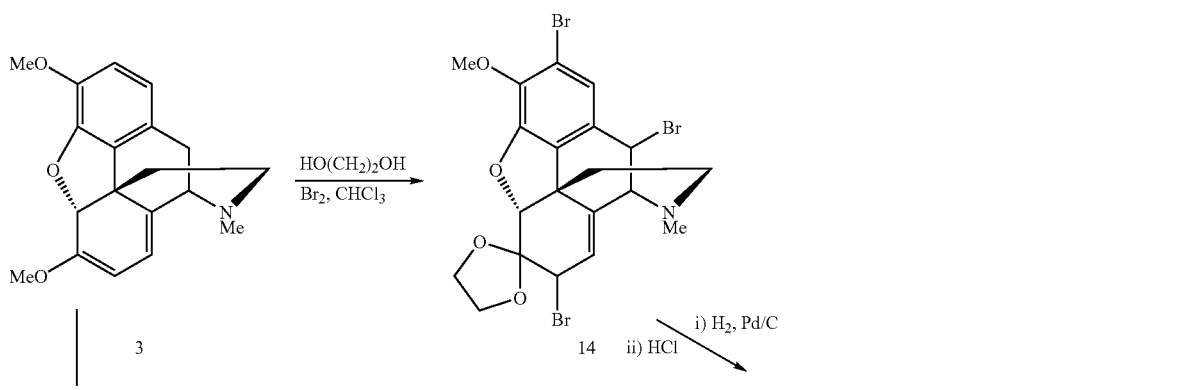

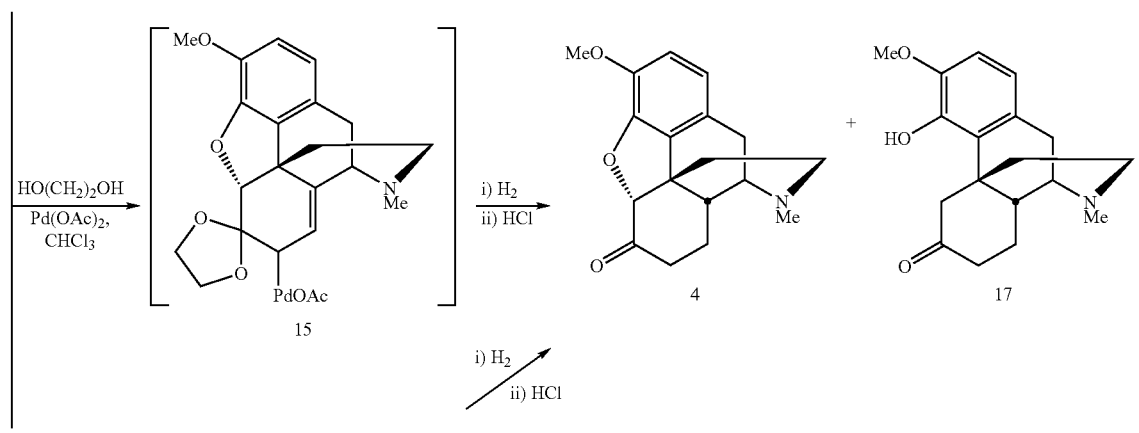

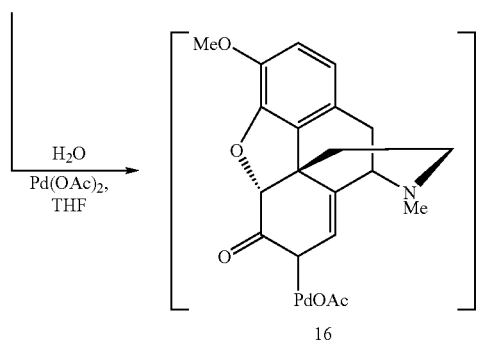

In one of the illustrated schemes, bromine is used as a 'pseudo-proton'. In the presence of ethylene glycol an intermediate, ketal 14 is formed. This ketal intermediate is, in turn, converted to hydrocodone by hydrogenation and hydrolysis. While bromine was used in this example, other "pseudo-protons" can also be used. For example, other halogens as well as metal catalysts can be substituted.

The previously unidentified β, γ, unsaturated ketals, such as neopinone ketals 10 and 14, are valuable intermediates for the synthesis of various opiate ketone derivatives not just hydrocodone. For example, ketal 10 can be used as a precursor to a C14 hydroxylated species, via functionalization of the olefin moiety. This methodology can be used to produce, for example, oxycodone or oxymorphone.

In a modified method of the invention shown above, the use of Pd(OAc)$_2$, in the presence of ethylene glycol provides the dual purpose of initially providing a proton surrogate and later acts as a hydrogenation catalyst. The intermediate 15 is rapidly converted to hydrocodone. Using this procedure hydrocodone was obtained in a one-pot sequence from thebaine.

In another variation of the method, thebaine is treated in aqueous THF with Pd(OAc)$_2$. This rapidly leads to the intermediate 16, which is immediately treated with 1 atmosphere of hydrogen to yield hydrocodone 4. This provides a rapid, efficient method for the production of hydrocodone from thebaine.

Although Pd(OAc)$_2$ was used in these reactions, it is apparent that other catalyst could also be used.

The present invention also provides a method for a one step conversion of thebaine to hydrocodone in the presence of a catalyst. The catalyst can be any metal from the platinum group (Ru, Rh, Pd, Os, Ir, Pt) which may or may not be on a solid support such as C, Al, Al$_2$O$_3$, SiO$_2$, etc. In a preferred embodiment, shown below, treatment of thebaine in an aqueous acid such as HCl or H$_2$SO$_4$ under about 1 atmosphere of hydrogen in the presence of Pd/C (10%) provides hydrocodone 4.

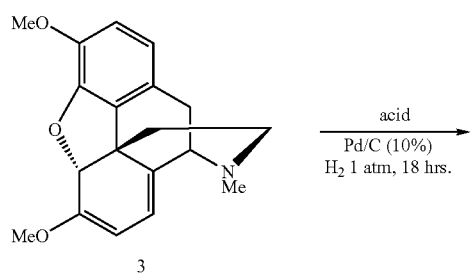

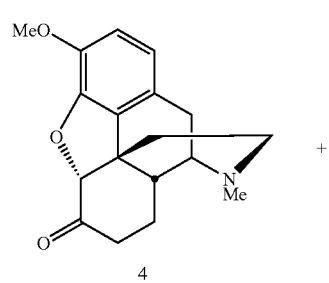

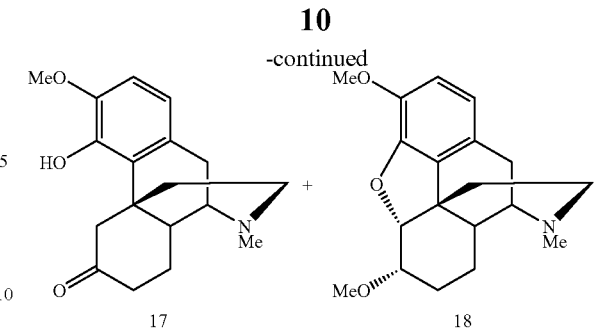

The above disclosure generally describes the present invention. It is believed that one of ordinary skill in the art can, using the preceding description, make and use the compositions and practice the methods of the present invention. A more complete understanding can be obtained by reference to the following specific examples. These examples are described solely to illustrate preferred embodiments of the present invention and are not intended to limit the scope of the invention. Changes in form and substitution of equivalents are contemplated as circumstances may suggest or render expedient. Other generic configurations will be apparent to one skilled in the art. All journal articles and other documents such as patents or patent applications referred to herein are hereby incorporated by reference.

EXAMPLES

Although specific terms have been used in these examples, such terms are intended in a descriptive sense and not for purposes of limitation. Methods of chemistry referred to but not explicitly described in the disclosure and these examples are reported in the scientific literature and are well known to those skilled in the art.

Example 1

Neopinone Ethylene Glycol Ketal (10)

Thebaine (500 mg, 1.6 mmol, 1.0 eq) was dissolved in CHCl$_3$ (0.9 ml) and ethylene glycol (1.0 g, 16.1 mmol, 10.0 eq) added. To this biphasic solution under vigorous stirring was added TsOH.H$_2$0 (1.0 g, 5.3 mmol, 3.3 eq). The reaction was heated to reflux for 45 minutes, cooled to 0° C. and the pH adjusted to >11 using saturated aqueous K$_2$CO$_3$ or ammonium hydroxide. Extraction of the reaction solution with CHCl$_3$ (5 ml×3), drying over Na$_2$SO$_4$ and filtration provided a dark yellow residue. Purification by silica gel chromatography (CHCl$_3$:MeOH:NH$_4$OH 98:2:1) provides the title product as a pale yellow oil in 38% yield.

FTIR ($v_{max}$ cm$^{-1}$) film: 3407, 3031, 2924, 2903, 2833, 2791, 1634, 1603, 1504, 1448, 1325, 1277, 1258, 1165, 1050, 1035, 825; $^1$H NMR (CDCl$_3$, 600 MHz): 6.74 (d, J=8.2 Hz, 1H), 6.64 (d, J=8.2 Hz, 1H), 5.56 (d, J=5.6 Hz, 1H), 4.70 (s, 1H), 4.28 (q, J=6.2 Hz, 1H), 3.93 (q, J=6.8 Hz, 1H), 3.86-3.90 (m, 4H), 3.81 (q, J=6.2 Hz, 1H), 3.64 (d, J=3.64 Hz, 1H), 3.26 (d, J=18.1 Hz, 1H), 2.67-2.78 (m, 2H), 2.61 (dd, J=12.6, 4.6 Hz, 1H), 2.50 (d, J=1.1 Hz, 1H), 2.47 (s, 3H), 2.14 (dd, J=16.2, 6.4 Hz, 1H), 2.06 (td, J=12.5, 5.0 Hz, 1H), 1.85 (dd, J=12.3, 1.9 Hz, 1H); $^{13}$C NMR (CDCl$_3$, 125.5 MHz): 145.6, 142.1, 138.4, 131.8, 127.2, 119.4, 113.8, 113.2, 108.1, 93.1, 66.7, 65.4, 61.2, 56.8, 45.9, 45.8, 42.2, 36.2, 32.7, 26.8; MS (EI) m/z (%): 342 (23.1), 341 (100.0), 326 (10.0), 269 (10.6), 268 (21.24), 255 (17.5), 254 (52.4), 240 (10.0), 226 (14.5), 212 (11.1), 85 (22.2), 83 (34.4), 42 (18.4); HRMS (EI) calcd for $C_{20}H_{23}NO_4$: 341.1627. found 341.1621.

Example 2

Dihydroneopinone Ethylene Glycol Ketal (13)

A solution of 10 (100 mg, 0.3 mmol) in $CHCl_3$ (1 ml) was treated with Pt/C (10%) under 1 atmosphere of $H_2$ for 16 hours. Filtration through a plug of silica with $CHCl_3$:MeOH: $NH_4OH$ 92:8:1 gave the title compound in quantitative yield.

FTIR ($v_{max}$ cm$^{-1}$) film: 2941, 2926, 2889, 1636, 1611, 1502, 1441, 1325, 1275, 1258, 1190, 1155, 1060, 922; $^1H$ NMR (CDCl$_3$, 600 MHz): 6.67 (d, J=8.2 Hz, 1H), 6.55 (d, J=8.2 Hz, 1H), 4.42 (s, 1H), 4.12 (q, J=6.5 Hz, 1H), 3.97 (q, J=5.0 Hz, 1H), 3.78-3.85 (m, 5H), 3.72 (q, J=6.3 Hz, 1H), 3.01-3.05 (m, 1H), 2.93 (d, J=18.3 Hz, 1H), 2.44 (dd, J=12.1, 4.3 Hz, 1H), 2.33 (s, 3H), 2.27 (dd, J=18.2, 5.4 Hz, 1H), 2.09-2.17 (m, 2H), 1.79 (dt, J=12.3, 4.9 Hz, 1H), 1.56-1.66 (m, 2H), 1.41-1.50 (m, 2H), 1.08 (td, J=12.7, 2.2 Hz, 1H); $^{13}C$ NMR (CDCl$_3$, 125.5 MHz): 146.6, 142.1, 129.2, 126.5, 118.6, 113.4, 108.6, 94.4, 66.4, 64.9, 59.5, 56.5, 47.1, 43.6, 42.9, 42.6, 36.5, 33.4, 22.3, 20.1; MS (EI) m/z (%): 344 (23.3), 343 (100.0), 342 (13.4), 329 (14.4), 256 (11.4), 244 (17.2), 198 (11.1), 99 (86.9), 59 (16.5), 55 (12.0); HRMS (EI) calcd for $C_{20}H_{25}NO_4$: 343.1784. found 343.1777.

Example 3

Hydrocodone (4) One pot Procedure from 10

A solution of 10 (45 mg, 0.13 mmol, 1.0 eq) in MeOH (90 µl) was treated with Pt/C (10%) under 1 atmosphere of $H_2$ for 12 hours. 25% v/v $H_2SO_4$/MeOH (0.5 ml) was added to the reaction solution, which was stirred for three hours. The pH of the solution was adjusted to >11 with saturated aqueous $K_2CO_3$ and extracted with $CHCl_3$ (5 ml×3). The combined organic extracts were dried over $Na_2SO_4$, filtered, concentrated and the crude material purified by column chromatography ($CHCl_3$:MeOH:$NH_4OH$—98:2:1) to yield hydrocodone in 75% yield.

All analytical data generated for hydrocodone synthesized in this manner is identical with that of an authentic sample of hydrocodone.

Example 4

One Pot Procedure from 3

Thebaine (100 mg, 0.32 mmol, 1.0 eq) was dissolved in THF (1 ml) and $H_2O$ (1 ml) added. To this solution Pd(OAc)$_2$ (72 mg, 0.32 mmol, 1.0 eq) was added. After two hours at room temperature the orange/red reaction solution contains no thebaine as evidenced by TLC. $H_2$ was added to the reaction vessel by use of a balloon and the reaction stirred for a further 4 hours. Removal of the balloon and filtration of the reaction through a plug of silica ($CHCl_3$:MeOH:$NH_4OH$ 92:8:1) gave the crude products 4 and 20 in a ratio of 1:1.34. Purification was achieved by column chromatography $CHCl_3$:MeOH:$NH_4OH$—98:2:1 to yield 4 in 43% and 20 in 52%.

All analytical data generated for hydrocodone synthesized in this manner is identical with that of an authentic sample of hydrocodone. Data for 20 is identical to that published in the literature.[11] β-dihydro-thebainone (20) FTIR ($v_{max}$ cm$^{-1}$) film: 3401, 2935, 2839, 2243, 1710, 1604, 1583, 1483, 1439, 1277, 1228, 1062, 922; $^1H$ NMR (CDCl3, 600 MHz): 6.68 (d, J=8.3 Hz, 1H), 6.60 (d, J=8.3 Hz, 1H), 4.25 (dd, J=13.3, 2.5 Hz, 1H), 3.82 (s, 3H), 3.13-3.16 (m, 1H), 2.98 (d, J=18.5 Hz, 1H), 2.76 (dd, J=18.5, 6.0 Hz, 1H), 2.60-2.64 (m, 1H), 2.46 (s, 3H), 2.41-2.45 (m, 1H), 2.31 (dt, J=12.8, 3.2 Hz, 1H), 2.23-2.28 (m, 2H), 2.12 (td, J=12.0, 4.1 Hz, 1H) 2.05 (s, 1H), 1.84-1.93 (m, 3H), 1.68 (qd, J=13.2, 5.0 Hz, 3H); $^{13}C$ NMR (CDCl$_3$, 125.5 MHz): 210.7, 145.1, 144.8, 129.7, 122.6, 118.5, 109.0, 57.0, 56.1, 50.4, 46.4, 44.3, 42.1, 41.0, 40.9, 38.0, 27.0, 23.8; MS (EI) m/z (%): 302 (11.6), 301 (56.2), 300 (18.0), 242 (10.3), 164 (53.3), 88 (11.2), 86 (64.3), 84 (100.0), 60 (19.3), 59 (16.7), 49 (19.7), 47 (23.5), 45 (24.7), 44 (13.3), 43 (34.7), 42 (17.8); HRMS (EI) calcd for $C_{18}H_{23}NO_3$: 301.1678. found 301.1671.

Example 5

1,7,10-tribromo-Neopinone ethylene glycol Ketal (14)

Thebaine (50 mg, 0.16 mmol, 1.0 eq) was dissolved in THF (1 ml) and ethylene glycol (100 mg, 1.61 mmol, 10.0 eq) added. Br$_2$ (103 mg, 0.64 mmol, 4.0 eq) was added in a single portion and the reaction stirred for 10 hours. Na$_2$SO$_3$ (sat. aq. solution) was added to remove excess bromine. Reaction cooled to 0° C. and the pH adjusted to >11 with saturated aqueous K$_2$CO$_3$. The reaction solution was extracted with CHCl$_3$ (5×5 ml), the organic extracts were combined and dried over Na$_2$SO$_4$. Chromatography of the crude residue with 200:1 CHCl$_3$:MeOH provides the title compound in 27% yield.

IR ($v_{max}$ cm$^{-1}$) film: 2391, 2937, 2891, 1654, 1632, 1611, 1487, 1435, 1287, 1203, 1160, 1125, 1089, 1051, 909; $^1H$ NMR (CDCl$_3$, 600 MHz): 6.92 (s, 1H), 5.88 (d, J=6.4 Hz, 1H), 5.25 (s, 1H), 4.61 (d, J=6.4 Hz, 1H), 3.94-3.99 (m, 1H), 3.88 (s, 3H), 3.81-3.87 (m, 1H), 3.61-3.64 (m, 1H), 3.11 (d, J=18.6 Hz, 1H), 3.04 (s, 3H), 2.70-2.79 (m, 1H), 2.56-2.68 (m, 2H), 2.50 (s, 3H), 2.37-2.43 (m, 1H), 1.76 (dd, J=12.8, 2.3 Hz, 1H); $^{13}C$ NMR (CDCl$_3$, 125.5 MHz): 145.2, 143.1, 132.3, 126.5, 117.0, 116.3, 112.0, 98.4, 92.0, 77.2, 64.4, 62.0, 60.1, 57.0, 49.5, 46.4, 45.3, 41.9, 35.1, 30.3; MS (EI) m/z (%): 344 (23.3), 343 (100.0), 342 (13.4), 329 (14.4), 256 (11.4), 244 (17.2), 198 (11.1), 99 (86.9), 59 (16.5), 55 (12.0); HRMS (EI) calcd for $C_{20}H_{25}NO_4$: 343.1784. found 343.1777.

Example 6

Pd/C Hydrogenation of Thebaine

Thebaine (100 mg, 0.32 mmol) was dissolved in 20% HCl (500 µl) and Pd/C (10%, 5 mg) added. The reaction was stirred under 1 atmosphere of H$_2$ at room temperature for 12 hours, after which time the reaction was basified with NH$_4$OH. The reaction mixture was extracted three times with CHCl$_3$ and the combined organic layers were dried over Na$_2$SO$_4$ and filtered. Column chromatography (CHCl$_3$:MeOH:NH$_4$OH 98:2:1) provided pure samples of hydrocodone, β-dihydrothebainone and tetrahydrothebaine in various ratios depending on the conditions applied.

One or more currently preferred embodiments have been described by way of example. It will be apparent to persons skilled in the art that a number of variations and modifications can be made without departing from the scope of the invention as defined in the claims.

REFERENCES a) Zezula, J.; Hudlicky, T. *Synlett,* 2005, 388 b), B. H.; Hudlicky, T.; Reed, J. W.; Mulzer, J.; Trauner, D. *Curr. Org.*

Chem. 2000, 4, 343-362 c) Butora, G.; Hudlicky, T. *Organic Synthesis: Theory and Applications*; Hudlicky, T., Ed.; JAI Press: Stamford, Conn., 1998; Vol. 4, pp 1-51. d) Hudlicky, T.; Butora, G.; Fearnley, S.; Gum, A.; Stabile, M. In *Studies in Natural Products Chemistry*; Atta-ur-Rahman, Ed.; Elsevier: Amsterdam, 1996; Vol 18, p 43

PHIL COX

PHIL COX a) Krassnig R.; Hederer, C.; Schmidhammer, H. *Arch. Pharm.,* 1996, 329, 325 b) Francis, C. A.; Lin, Z.; Kaldahl, C. A.; Antczak, K. G.; Kumar, V.; US 2005/0038251 A1 c) Casner, M. L.; Dung, J. S.; Keskeny, E. M.; Luo, J. US 2006111383. Alternative methods for C-14 hydroxylation include a photochemical approach: López, D.; Quiñoá, E.; Riguera, R. *J. Org. Chem.,* 2000, 65, 4671-4678

ICH safety guidelines (ICH S2A, 1995; ICH S2B, 1997).

Barber, R.; Rapoport, H.; *J. Med. Chem.,* 1976, 19, 1175-1180

Dauben, W. G.; Baskin, C. P.; Van Riel, H. C. H. A. *J. Org. Chem.,* 1979, 44, 1567-9

Heathcock, C. H.; Ratcliffe, R. *J. Am. Chem. Soc.,* 1971, 93, 1746-1757

For examples see: a) Conroy, H. *J. Am. Chem. Soc.* 1955, 77, 5960-5966 b) Batterham, T. J.; Bell, K. H.;

Weiss, U. *Aust. J. Chem.,* 1966, 19, 321-327 and references cited therein

This work is based on a brief report in DE 441613

Moos, W. H., Gless, R. D., Rapoport, H. J., *J. Org. Chem.,* 1983, 48, 227

What is claimed is:

1. A method of converting thebaine to a morphine derivative selected from the group consisting of hydrocodone and hydrocodone-related compounds as defined by general formula (1),

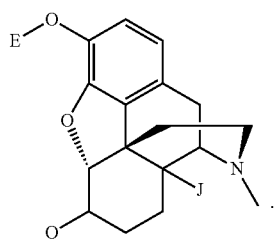

(1)

wherein E is H or CH$_3$, G is O and J is H or OH,
said method comprising the steps of:
a. Combining thebaine with an organic compound having at least one hydroxyl group in the presence of a catalyst to obtain a ketal intermediate;
b. exposing the ketal intermediate to hydrogenation to obtain a hydrogenated intermediate; and
c. hydrolyzing the hydrogenated intermediate to obtain the morphine derivative.

2. A method according to claim 1, wherein the morphine derivative is selected from the group consisting of hydrocodone, hydromorphone, oxycodone, and oxymorphone.

3. A method according to claim 2, wherein the morphine derivative is hydrocodone.

4. A method according to claim 1, wherein the hydrogenation and hydrolyzation steps are combined in a one-pot procedure.

5. A method according to claim 1, wherein the organic compound is an aliphatic alcohol other than methanol.

6. A method according to claim 1, wherein the organic compound is a diol.

7. A method according to claim 6, wherein the diol is ethylene glycol.

8. A method according to claim 6, wherein the diol is 2,3-dimethyl-1,4-butane diol.

9. A method according to claim 1, wherein the catalyst is a protic or Lewis acid.

10. A method according to claim 7, wherein the catalyst is p-toluenesulfonic acid.

11. A method according to claim 1, wherein the catalyst is a metal catalyst.

12. A method according to claim 11, wherein the catalyst is selected from the group consisting of Pd, Pd(OAc)$_2$, PdCl$_2$, PdBr$_2$, PdO, RhCl$_3$, PtO$_2$, RhCl(PPh$_3$)$_3$, Rh/Al, Pd/C, Pt/C, Pd on CaCO$_3$/Pb, Pd/Al, PtCl$_2$, PtCl$_4$, Al, Zn, Fe, Sn, Ru, Co, Rh, Ir, Ni, Pd, Pt, Ti, Os, and Cu.

13. A method according to claim 12, wherein the catalyst is selected from the group consisting of Pd(OAc)$_2$, PdCl$_2$, PdBr$_2$, PdO, RhCl$_3$, PtO$_2$, RhCl(PPh$_3$)$_3$, Rh/Al, Pd/C, Pt/C, Pd on CaCO$_3$/Pb (Lindlar), Pd/Al, PtCl$_2$, and PtCl$_4$.

14. A method according to claim 12, wherein the catalyst is selected from the group consisting of Al, Zn, Fe, Sn, Ru, Co, Rh, Ir, Ni, Pd, and Pt.

15. A method according to claim 12, wherein the catalyst is selected from the group consisting of Ti, Os, and Cu.

16. A method of obtaining a morphine derivative from thebaine, wherein said morphine derivative is selected from the group consisting of hydrocodone and hydrocodone-related compounds as defined by general formula (1),

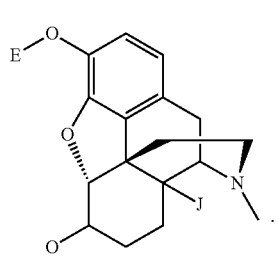

(1)

wherein E is H or CH$_3$, G is O and J is H or OH,
said method comprising:
a. combining thebaine with an organic compound having at least one hydroxyl group in the presence of a pseudo-proton to obtain a ketal intermediate; and
b. subjecting the intermediate to a one pot hydrogenation and hydrolysis to obtain the morphine derivative.

17. A method according to claim 16, wherein the pseudo proton is provided by a halogen.

18. A method according to claim 17, wherein the halogen is selected from the group consisting of bromine, chlorine and iodine.

19. A method according to claim 18, wherein the halogen is bromine.

20. A method according to claim 16, wherein the pseudo proton is provided by a transition metal catalyst.

21. A method according to claim 16, wherein the morphine derivative is hydrocodone, hydromorphone, oxycodone or oxymorphone.

22. A method according to claim 21, wherein the derivative is hydrocodone.

23. A one pot method of obtaining hydrocodone from thebaine comprising exposing thebaine to Pd(OAc)$_2$ in the presence of an organic compound having at least one hydroxyl group.

24. A method according to claim 23, wherein the organic compound having at least one hydroxyl group is ethylene glycol.

25. A one pot method for the conversion of thebaine to hydrocodone comprising exposing thebaine to Pd(OAc)$_2$ in the presence of aqueous THF followed by hydrogenation.

26. A one pot method for obtaining hydrocodone from thebaine comprising exposing thebaine to an acid under about one atmosphere of hydrogen in the presence of a catalyst under aqueous conditions.

27. The method of claim 26, wherein the acid comprises HCl or H$_2$SO$_4$.

* * * * *